United States Patent [19]

Johnson et al.

[11] Patent Number: 5,507,726
[45] Date of Patent: Apr. 16, 1996

[54] PERFUSION CATHETER WITH MOVING TUBE

[75] Inventors: Kirk L. Johnson, Miami Lakes; Mark N. Inderbitzen, Miramar, both of Fla.

[73] Assignee: Cordis Corporation, Miami Lakes, Fla.

[21] Appl. No.: 212,975

[22] Filed: Mar. 15, 1994

[51] Int. Cl.$^6$ ............................................. A61M 25/00
[52] U.S. Cl. ............................................. 604/96
[58] Field of Search ............................. 604/101, 280, 604/96, 264, 191–194

[56] References Cited

U.S. PATENT DOCUMENTS

| | | |
|---|---|---|
| 4,581,017 | 4/1986 | Sahota . |
| 4,723,549 | 2/1988 | Wholey et al. . |
| 4,771,777 | 9/1988 | Horzewski et al. . |
| 4,820,271 | 4/1989 | Deutsch . |
| 4,944,745 | 7/1990 | Sogard et al. . |
| 5,035,694 | 7/1991 | Kasprzyk et al. . |
| 5,063,018 | 11/1991 | Fontirroche et al. . |
| 5,152,277 | 10/1992 | Honda et al. . |
| 5,179,161 | 1/1993 | Littleford et al. ............ 604/96 |
| 5,195,971 | 3/1993 | Sirhan . |
| 5,295,961 | 3/1994 | Niederhauser et al. .......... 604/96 |

*Primary Examiner*—C. Fred Rosenbaum
*Assistant Examiner*—Manuel Mendez
*Attorney, Agent, or Firm*—Gerstman, Ellis & McMillin, Ltd.

[57] ABSTRACT

An intravascular balloon catheter comprises a catheter body having a proximal end a distal end, and a balloon carried adjacent the distal end. The catheter body defines an inflation lumen which extends along essentially the length of the body proximal to the balloon and which communicates with the interior of the balloon. The catheter body also defines a second lumen having an open, distal end and extending at least most of the length of the body. A first tube, aligned with the second lumen, extends through the balloon and is open at both ends. A portion of the catheter body which defines the second lumen is longitudinally slidable relative to the balloon and the first tube between an advanced position and a retracted position. In the advanced position the second lumen and tube are together to allow advancement of a guidewire through both the second lumen and the first tube. In the retracted position, the second lumen is spaced from the first tube, so that the first tube is open to receive blood flow therethrough from its open proximal end.

20 Claims, 1 Drawing Sheet

PERFUSION CATHETER WITH MOVING TUBE

BACKGROUND OF THE INVENTION

In balloon angioplasty or PTCA, a catheter is advanced through the arterial system of a patient to an area of stenosis where an artery is partially or completely blocked. The catheter, with the balloon deflated, is advanced through the stenotic area, and then the balloon is inflated to expand the stenosis.

With conventional catheters for angioplasty, the blood flow is completely blocked while the balloon is inflated. This tends to limit the amount of time that the inflation of the balloon can be tolerated by the patient.

Thus, in Sahota U.S. Pat. No. 4,581,017; Sogard et al. U.S. Pat. No. 4,944,745 and Horzewski et al. U.S. Pat. No. 4,771,777, among others, balloon catheters for angioplasty are disclosed in which the balloon can be inflated without completely blocking the blood flow through the artery in which the balloon is inflated. However, in the prior art designs, the flow capacity of blood through the inflated balloon may be undesirably low and/or may be undesirably turbulent for the handling of blood. Also, difficulties may be encountered in some of the prior art designs with respect to the advancement of the guidewire, because of the presence of a side aperture through which the guidewire may accidentally project during advancement.

In accordance with this invention, an intravascular balloon catheter is provided which addresses the above problems. A guidewire may be reliably advanced through the catheter of this invention without risk of the guidewire projecting laterally out of a side aperture in the catheter, thus becoming stuck and non-advanceable. Additionally, the catheter of this invention can provided a relatively laminar, non-turbulent, high volume flow of blood through an inflated balloon in an artery when that is required. At the same time, this flow of blood may be shut off when the guidewire or the catheter are being advanced, and then reopened at any desired time for selective and beneficial clinical advantage.

DESCRIPTION OF THE INVENTION

By this invention, an intravascular balloon catheter is provided which comprises a catheter body having a proximal and a distal end, and having a balloon carried adjacent the distal end. The catheter body defines an inflation lumen which extends along essentially the length of the body proximal to the balloon, and which communicates with the interior of the balloon. The catheter body also defines a second lumen having an open distal end and extending along at least most of the length of the body. A first, perfusion tube is also provided, being aligned with the second lumen, and extending through the balloon. The first tube is then open at both ends to serve as a route for blood to pass through the inflated balloon.

In accordance with this invention, a portion of the catheter body which defines the second lumen is longitudinally slidable relative to the balloon and the first tube between an advanced position and a retracted position. In the advanced position, the second lumen and first tube are positioned together, to facilitate the advancement of a guidewire through both the second lumen and the first tube. In the retracted position, the second lumen is spaced from the first tube. The first tube is then open to receive blood flow therethrough, while the catheter occupies a blood vessel and the balloon is in its expanded condition. This avoids interruption of blood flow through the blood vessel.

In the preferred embodiment, the catheter body comprises an outer portion which defines the inflation lumen and a guidewire lumen spaced from and parallel to the inflation lumen, both lumens being defined within the outer portion, which is typically in fixed position relative to the catheter balloon and first lumen. The second lumen and the slidable portion are, in turn, defined by a sliding tube or sleeve which is positioned in slidable relation within the guidewire lumen. The sliding tube, which may be of circular cross section, may be advanced and retracted in sliding relation between the advanced and the retracted positions discussed above. In the advanced position, the sliding tube may be long enough to extend through the first tube and out the distal end thereof to serve as the catheter tip. In the retracted position, the first tube is open and free at both ends, permitting the flow of blood therethrough.

A significant advantage is achieved by the above described feature of using the sliding tube in its advanced position as the catheter tip. In certain prior art catheters, the perfusion tube extending through the balloon needs to have a diameter that is greater than the outer diameter of the guidewire to provide adequate blood flow capacity across the balloon while the balloon is inflated. Because of this large diameter, the distal end of the perfusion tube, which serves as the catheter tip, must be tapered, and side holes must be located in the tapered end of the perfusion tube to increase the blood flow capacity. Such a tapered tip typically extends about 0.4 to 0.5 inch past the distal end of the balloon. This may be a problem, because it extends farther than physicians would like but is necessary to achieve proper tapering of the catheter tip to avoid "coring" of tissue, which is of course very undesirable. Also, the side holes defined by the tapered end tend to weaken it. As another disadvantage, the guidewire can actually penetrate out through the side holes because of such weakening, which may result in cracking or enlargement that permits such penetration. This also is very undesirable.

By this invention, a sliding sleeve not only serves as a more reliable track for the guidewire, being free of side holes, but it eliminates the need for a long, tapered tip. By this invention, the sliding sleeve can project about 0.1 inch or less beyond the perfusion tube. However, since the sliding sleeve preferably has an outer diameter that is almost as large as the inner diameter of the perfusion tube, coring can be eliminated.

Since the sliding sleeve receives the guidewire in its lumen, at least the inner lumen surface of the sleeve will preferably be made of a lubricating material such as PTFE. It may also be desirable for at least the distal tip of the sliding sleeve to be made of a softer material than the perfusion tube material to provide a soft tip to the catheter.

In an alternative embodiment of the catheter of this invention, the catheter body may comprise a second tube, fixed to the first, perfusion tube, and which defines the inflation lumen. The second lumen and the slidable catheter portion are then defined by a sliding body which is slidable along the second tube.

DESCRIPTION OF SPECIFIC EMBODIMENTS

Figure 1:
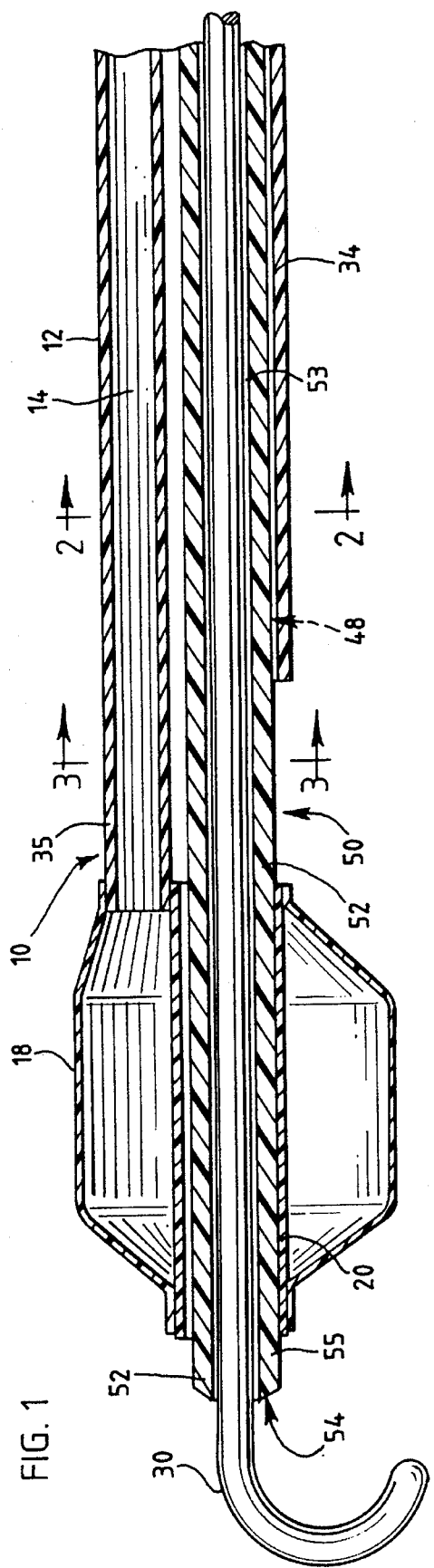
FIG. 1 is a longitudinal sectional view of the distal end of a preferred embodiment of the catheter of this invention, shown in its advanced position.
Figure 2:
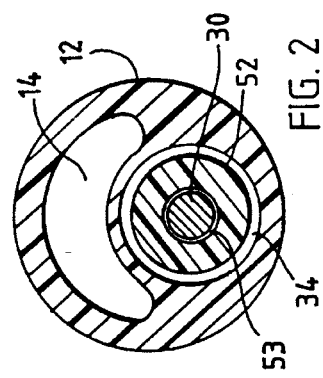
FIG. 2 is a sectional view taken along line 2—2 of FIG. 4.
Figure 3:
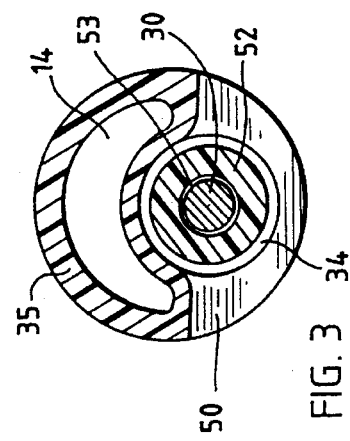
FIG. 3 is a sectional view taken along line 3—3 of FIG. 1.

Referring to FIGS. 1 and 2, catheter 10 comprises an outer catheter body portion 12 which is secured to a balloon 18 and a first tube 20 which supports the balloon. Outer catheter body portion 12 is fixed in this embodiment with respect to balloon 18 and first tube 20. Tube 20 is open at both ends to provide an access through the inflated balloon 18. Body portion 12 defines an inflation crescent or kidney-shaped lumen 14 and another guidewire lumen 34. Outer catheter body portion 12 may be made from an extruded plastic material, for example in accordance with the teachings of Fontirroche U.S. Pat. No. 5,063,018, with a distal end portion 35 of body portion 12 surrounding lumen 14, but terminating about lumen 34 so that open space 50 is defined.

The proximal end of catheter 10 may be conventional, having a standard Y-shaped two lumen hub connected to lumens 14, 34.

Guidewire 30 is shown to be extending entirely through the catheter. The guidewire may be so advanced without any problem of accidentally projecting laterally out of open space 50 because of the presence of inner, sliding tube 52, which may be of generally circular cross section, and defines a second lumen 53, and which occupies both the guidewire lumen 34 and the lumen of first tube 20, as shown.

Sliding tube 52 traverses the open space 50, so that a guidewire 30 advancing through sliding tube 52 is advanced with great ease. Also, catheter 10 can be advanced with great ease in the same configuration along guidewire 30.

Particularly, sliding tube 52 can project distally outwardly from first tube 20 and balloon 18 as shown in FIG. 1 to serve as the tip of the catheter, to achieve the advantages previously discussed. Distal end 54 of sliding tube 52 can serve the needed function of providing a blunt end of reduced diameter for the catheter, to prevent coring and to otherwise facilitate catheter advancement through a blood vessel system. However, when catheter 10 has been positioned in its desired position in the blood vessel system, guidewire 30 and sliding tube 52 may be withdrawn to a point which is proximal of the open space 50, for example to point 48. In that configuration, both ends of first tube 20 are open for the flow of blood through balloon 18, while balloon 18 is inflated in an angioplasty procedure.

Thus, because of the open characteristic of space 50, being preferably open on at least three sides in this embodiment, and the open-ended, tubular characteristic of tube 20, a smooth, generally laminar flow of blood can be provided at higher flow rates during balloon inflation episodes. This permits a longer period of balloon inflation without causing ischemia and with less damage to blood cells.

Balloon 18 is shown to be a tube, sealed at its distal end to first tube 20 and at its proximal end to tube 20 and the portion of catheter body 12 that defines inflation lumen 14. It can be seen that the kidney-shaped cross-section of inflation lumen 14 facilitates the hermetic sealing of balloon 18 about that area of complex structure. However, if desired, an added sealing and reinforcing member of appropriate shape may be provided in that area.

Typically the inner diameter of both first tube 20 and the guidewire lumen 34 is about 0.03 inch. The outer diameter of sliding sleeve 52 may be about 0.028 inch, for easy sliding through both lumens. Sliding sleeve 52 has an inner diameter for example of about 0.016 inch for a 0.014 inch guidewire or 0.02 inch for a 0.018 inch guidewire. This provides proper spacing of the desired guidewire 30.

The length of space 50 is preferably no less than the inner diameter of first tube 20, to be sure there is adequate access to flowing blood, to achieve the maximum blood flow that first tube 20 can handle. Specifically, the length of space 50 may be about 0.03 to 0.06 inch.

A portion 55 of sliding tube 52 which incorporates tapered distal end 54 thereof may be made of a material which is softer than the remainder of sliding tube 52. This may comprise a tubular end piece which is thermally or otherwise sealed to the remainder of sliding tube 52.

Thus, the catheter of FIGS. 1 and 2 exhibits the advantage that it does not require a permanently affixed, internally tapered tip, which, in turn, requires side holes for increased flow. The inner sliding tube 52 can provide a suitable catheter distal tip, but which permits, upon withdrawal of tube 52 and guidewire 30, a significantly improved volume and pattern of flow through tube 20.

The above has been offered for illustrative purposes only, and is not intended to limit the scope of the invention of this application, which is as defined in the claims below.

That which is claimed is:

1. An intravascular balloon catheter, which comprises:

a catheter body having a proximal end and a distal end, and having a balloon carried adjacent said distal end; said catheter body defining an inflation lumen which extends along a length of said body proximal to said balloon and which communicates with the interior of said balloon, said catheter body also defining a second lumen having an open, distal end and extending along a length of said body;

a first tube, substantially coaxially aligned with said second lumen, said first tube extending along said balloon and open at both ends, a portion of said catheter body which defines said second lumen being longitudinally slidable relative to said balloon and first tube between an advanced position in which the second lumen and first tube are together to allow advancement of a guidewire through both said second lumen and first tube, and a retracted position in which the second lumen is spaced from said first tube, whereby said first tube is open to receive blood flow therethrough.

2. The catheter of claim 1 in which said catheter body comprises an outer portion which defines said inflation lumen and a guidewire lumen spaced from and parallel to said inflation lumen, said second lumen and slidable catheter portion being defined by a sliding tube which is positioned in slidable relation within said guidewire lumen.

3. The catheter of claim 2 in which said guidewire lumen is at least about the same diameter as the first tube.

4. The catheter of claim 2 in which said inflation lumen is crescent-shaped in cross section.

5. The catheter of claim 2 in which said sliding tube is long enough to extend fully through said first tube to provide a narrowed catheter distal tip in the advanced position.

6. An intravascular balloon catheter which comprises a catheter body having a proximal end and a distal end, and a balloon carried adjacent said distal end, said catheter body defining an inflation lumen which extends along a length of said body proximal to said balloon and which communicates with the interior of said balloon, said catheter body also defining a guidewire lumen extending parallel along said catheter with said inflation lumen, a portion of said catheter body which defines said guidewire lumen terminating to define a space adjacent to and proximal of said balloon and an open, distal end; a first tube, aligned with and longitudinally spaced from said guidewire lumen, said first tube extending along said balloon and open at both ends; a sliding tube, positionable within said guidewire lumen and long enough to extend from the catheter proximal end at least to said first tube, whereby said sliding tube may occupy an advanced position of engagement with said first tube, with the sliding tube passing across said space to facilitate guidewire advancement through the catheter, and said sliding tube can occupy a retracted position in which said sliding tube is proximal to said space to allow blood to flow through said space and distally along said balloon through said first tube.

7. The catheter of claim 6 in which said sliding tube is of a length sufficient in said advanced position to permit the distal end of said sliding tube to project distally beyond the remainder of said catheter, to serve as a narrowed, blunt tip thereof during catheter advancement.

8. The method of performing balloon angioplasty with a catheter, which comprises advancing the catheter through the blood vessel of a patient along a guidewire which extends through a lumen of the catheter, to bring a balloon of said catheter into a desired position within said blood vessel; moving a movable portion of said catheter to open a first tube extending along said balloon; withdrawing said guidewire to a retracted position proximal of said first tube; inflating said balloon; and allowing blood to flow from end-to-end through said first tube, to reduce the interruption of blood circulation through the blood vessel while the balloon is inflated.

9. The method of claim 8 in which the balloon is thereafter deflated; the movable portion of said catheter is moved to close said first tube; and said guidewire is advanced completely through said catheter.

10. The method of claim 8 in which said movable catheter portion is a slidable sleeve positioned within a guidewire lumen of the catheter, said guidewire lumen being proximally spaced from said first tube.

11. The method of claim 10 in which, when said slidable sleeve is initially positioned within said first tube to close said first tube, said slidable sleeve projects distally beyond any other portion of the catheter to serve as a blunt, reduced-diameter catheter tip.

12. The method of claim 8 in which the balloon is thereafter deflated; the movable portion of said catheter is moved to close said first tube; and said guidewire is advanced completely through said catheter, in which said movable catheter portion is a slidable sleeve positioned within a guidewire lumen of the catheter, said guidewire lumen being proximally spaced from said first tube.

13. The method of claim 12 in which, when said slidable sleeve is initially positioned to close said first tube, said slidable sleeve projects distally beyond any other portion of the catheter to serve as a blunt, reduced-diameter catheter tip.

14. An intravascular balloon catheter, which comprises:
a catheter body having a proximal end and a distal end, and having a balloon carried adjacent said distal end; said catheter body defining an inflation lumen which extends along a length of said body proximal to said balloon and which communicates with the interior of said balloon, said catheter body also defining a guidewire lumen having an open distal end proximal of said balloon and extending along a length of said body;

a first tube, aligned with said guidewire lumen, said first tube extending along said balloon and open at both ends; and a longitudinally sliding sleeve, positioned within and slidable in said guidewire lumen, said sliding sleeve being capable of sliding in the guidewire lumen between a retracted position in which the sliding sleeve is proximally spaced from said first tube and balloon and an advanced position in which said sliding sleeve projects distally through said first tube beyond said balloon to serve as a catheter tip.

15. The catheter of claim 14 which is free of a tapered, distal catheter tip.

16. The catheter of claim 14 in which said catheter body defines an open space immediately proximal of said balloon, said open space communicating with the proximal end of said first tube.

17. The catheter of claim 14 in which said sliding sleeve defines a distal end which is made of a material softer than proximal portions of said sleeve.

18. An intravascular balloon catheter, which comprises: a catheter body having a proximal end and a distal end, and having a balloon carried adjacent said distal end; said catheter body defining an inflation lumen which extends along a length of said body proximal to said balloon, and which communicates with the interior of said balloon, said catheter body also defining a guidewire lumen;

a first tube, aligned with and longitudinally spaced from said guidewire lumen, said first tube extending along the balloon and open at both ends, said catheter body comprising an outer portion which defines said inflation lumen and said guidewire lumen spaced from and parallel to said inflation lumen, and a sliding tube positionable in slidable relation within said guidewire lumen, said sliding tube defining a second lumen and being slidable between an advanced position in which the second lumen and first tube are together to allow advancement of a guidewire through both the second lumen and first tube, and a retracted position in which the sliding tube and second lumen are spaced from said first tube, whereby said first tube is open to receive blood flow therethrough, said sliding tube being long enough to extend fully through said first tube to provide a narrowed catheter distal tip in the advanced position, said inflation lumen being non-circular in cross section.

19. The catheter of claim 18 in which said guidewire lumen is at least about the same diameter as the first tube.

20. The catheter of claim 19 in which said sliding tube defines a distal end which is made of a material softer than proximal portions of said sliding tube.

* * * * *